United States Patent [19]

Disharoon

[11] Patent Number: 4,485,706

[45] Date of Patent: * Dec. 4, 1984

[54] METHODS AND APPARATUS FOR CUTTING A SUBSTRATE

[76] Inventor: Dale R. Disharoon, 2480 Newcastle Ave., Cardiff, Calif. 92007

[*] Notice: The portion of the term of this patent subsequent to May 26, 1998 has been disclaimed.

[21] Appl. No.: 353,019

[22] Filed: Mar. 1, 1982

Related U.S. Application Data

[60] Continuation-in-part of Ser. No. 201,131, Oct. 27, 1980, Pat. No. 4,317,401, which is a division of Ser. No. 56,469, Jul. 11, 1979, Pat. No. 4,269,092.

[51] Int. Cl.³ .............................................. G01N 1/06
[52] U.S. Cl. ......................................... 83/42; 30/350; 76/101 R; 83/856; 83/915.5; 128/305.1
[58] Field of Search .................. 83/42, 651, 856, 701, 83/915.5; 76/101 R; 30/350; 225/2; 128/305, 305.1

[56] References Cited

U.S. PATENT DOCUMENTS

| 3,803,958 | 4/1974 | Fernandez-Moran | 83/915.5 |
| 4,051,755 | 10/1977 | Raveed | 83/915.5 |
| 4,269,092 | 5/1981 | Disharoon | 83/915.5 |
| 4,317,401 | 3/1982 | Disharoon | 83/915.5 |

Primary Examiner—James M. Meister
Attorney, Agent, or Firm—Fitch, Even, Tabin & Flannery

[57] ABSTRACT

Methods and apparatus utilizing a vitreous carbon knife element having particular properties for smoothly cutting a substrate such as a tissue substrate for microtomy or during surgical procedures such as ophthalmolgic or heart surgery.

10 Claims, 11 Drawing Figures

METHODS AND APPARATUS FOR CUTTING A SUBSTRATE

This application is a continuation in part of my application Ser. No. 201,131 filed Oct. 27, 1980, now U.S. Pat. No. 4,317,401, which is a division application of application Ser. No. 56,469 filed July 11, 1979, now U.S. Pat. No. 4,269,092, which are incorporated by reference herein.

The present invention is directed to methods and apparatus for cutting substrates and, more particularly, is directed to methods and apparatus for controllably slicing substrates such as tissue samples for microscopic examination, and tissues in a living body during surgical procedures.

The main principles of ultramicrotomy were adapted from light microscopy. However, major modifications had to be made with respect to embedding procedures, the manufacture of knives and the construction of microtomes. Much of this development has been the result of empirical work and many details of well known steps in conventional sectioning procedures are not fully understood in theory.

In conventional sectioning procedures for sample sectioning, frozen tissue samples, or tissue samples embedded in either a rigid or semi-solid organopolymeric matrix are rapidly cleaved by means of a microtome sectioning knife. In order to produce sections of specimen suitable for ultramicroscopic examination, marks on the specimen due to knife edge defects or deformations, should be minimized, and the knife edge should function to cleave the specimen cleanly. The quality of microtome sections depends to a large extent on the quality and characteristics of the microtome knife, and the cutting process is also influenced by properties of the trough fluid used in the sectioning and sectioned sample transport operations.

Metallic knives such as steel microtome knives were originally used for cutting sections for ultramicroscopic examination by techniques such as electron microscopy. However, the use of steel microtome knives is cutting sections for electron microscopes has substantial disadvantages, especially in the achievement of satisfactory sample surfaces for examination and in the provision and maintenance of sufficiently sharp knife edges. Substantial effort has been expnded in the art to overcome such difficulties and to provide cutting methods utilizing materials having suitable homogeneity and hardness without excessive brittleness. One significant result of such development efforts has been the provision of cleaving methods for providing and using glass "knives" by breaking glass sheets to produce a cleaved cutting edge [Latta, et al., *Use of a Glass Edge in Tissue Sections for Electron Microscopy*, Proc. Bio. Med., Vol. 74, pp. 436–439 (1950]. By providing a series of straight parallel scorings at 90° to the long axis of a glass strip, with one central portion of each 2" distance kept free of score marks, 1" glass blocks may be produced that can then be cleaved at a 45° angle (to score-mark free corner) thus producing a knife edge length along the thickness dimension of one surface of one triangle (1"×1"×¼") and a less perfect edge on one edge of the opposite triangle. However, while such glass knives represent a substantial improvement in the art, such cleaved edges can be used only for a limited time, and for providing a limited number of sectioned samples.

In view of the tendency of such cleaved edges to lose their properties with time and/or use, glass microtome knives are conventionally made on site as needed under conditions of use. In this latter connection, specific jigs have been developed for producing precision glass knives for laboratory applications, specifically for cleaving tissue samples for microscopy. Examples of such devices are disclosed in U.S. Pat. Nos. 3,207,398, 3,494,521 and 3,908,878.

The use of glass knives in microtomy suffer from a number of disadvantages. They may be time consuming to produce and, because glass is physically a super cooled liquid, have a very short life. The cleaved edges produced by the intersection of the fracture plane with another plane at a score-free junction may be sharp initially, but within a matter of hours and without use, the edge will begin to dull due to flow characteristics of the glass, and/or its inability to maintain the precise molecular arrangement that exists at the cleaving edge immediately after breaking. Such knives, as indicated, must therefore be produced at the point of application since their structural longevity is no more than a day or two in their sharpest state. In addition to such limitation, glass knives dull quickly in use and may be utilized only with difficulty in providing numerous thick sections of hard specimens including routinely embedded materials.

In this regard, not only is it desirable to produce thin sections of hard samples, it is frequently desirable to prepare samples for ultramicroscopic examination by cleaving relatively thick sections of the specimen material embedded in an organopolymeric material, such as a specimen having a thickness in the range of 10 to 50 microns, and to reorient and reembed the thick specimen at a different angle. The reembedded specimen may then be subsequently sectioned to provide the desired specimen. Glass knives function best when cleaving sections are no more than 2 microns in thickness, but may be utilized to provide a very limited number of sections per knife when a thickness of about 2 to about 10 microns is desired. Thicker sections may not reliably be provided through the use of glass knives.

In an attempt to overcome the general thin and thick sectioning limitations of glass knives, knife edges of harder crystalline materials such as diamond have been proposed for microtomy purposes [Fernandez-Moran, A.H., *A Diamond Knife for Ultra Thin Sectioning*, Exp. Cell Research, 5, pp. 255–256 (1953)], and subsequently have achieved substantial commercial application. However, diamond knives are very expensive and difficult to produce thereby limiting their general applicability. Further, diamond knife edges are fragile, and sensitive to impacts and small blows, so that a knife being used for thick sectioning has a shorter life than one being used for thin sectioning. The economic risk of various sample materials represents a substantial limitation in the use of diamond knives.

Because of the expense and fragility of diamond knives, various efforts have been made to improve the cutting qualities and longevity of relatively inexpensive glass knives. For example, efforts have been made to coat glass knives with materials such as tungsten in an effort to overcome deficiencies of glass [Roberts, *Tungsten Coating—A Method of Improving Glass Microtome Knives for Cutting Ultrathin Sections, Journal of Microscopy*, Vol. 103, Pt. 1, pp. 113–119 (1974)]; but such techniques have not achieved wide acceptance. Still others [Ward, *Some Observations on Glass Knife Making*, Stain Technology, Vol. 52, pp. 305<309 (1977)], have tried varying the bevel angle, up to 55°, of the glass knife edge to enhance cleaving capabilities, but succeed only to a limited degree.

However, despite significant need for improved microtomy methods and apparatus, there have been few significant developments in respect of glass microtomy knives since their introduction in 1950, and glass and diamond microtomy systems remain as the two principal alternatives available for ultramicroscopic sample sectioning.

Similarly, there is a need for improved surgical apparatus and procedures for cutting living tissue to controllably and repeatedly produce a smooth, clean incision in the tissue. In this regard, for example, in surgery, such as opthalmologic surgery, heart surgery, and various microsurgical procedures, it is necessary to cut relatively tough substrate tissues in a precisely controlled manner. It is desirable that the respective living tissues subjected to the surgical procedure be smoothly and reproduceably cut in a single stroke with a minimum of applied cutting force and a minimum of tissue trauma, to achieve the necessary surgical incision. Accordingly, there is a need for improved methods and apparatus for cutting of substrates requiring a smooth clean incision surface such as living and non-living tissue, and it is an object of the present invention to provide such methods and apparatus.

These and other objects of the invention will become apparent from the detailed description and accompanying drawings of which.

Generally in accordance with the present invention, methods and apparatus for cleanly slicing substrate materials are provided utilizing knife elements of particular design and composition, particularly including surgical methods which utilize such vitreous carbon knife elements.

In this connection, knife elements may be provided in accordance with the present invention which comprises a vitreous carbon body of particular physical property parameters, and having two intersecting substantially smooth surfaces which intersect along a substantially microscopically smooth intersection edge. For blade elements such as microtome knives which will have substantial force applied to the knife edge during use, the edge-forming surfaces should best intersect at an angle in the range of from about 35° to about 60°, and preferably in the range of from about 40° to about 50°, to form a high performance microtome knife edge. For blade elements such as scalpels and other surgical knives which are utilized in surgery on living tissue, the facet bevel angle may be more acute, such as in the range of from about 7° to about 35°, and preferably about 17° plus or minus about 8°. At least one of the intersecting surfaces adjacent the knife edge may be provided with a hydrophilic surface, as will be described in more detail hereinafter.

As indicated, the vitreous carbon knife element utilized in accordance with the present invention comprises a vitreous carbon body. Though polymeric carbon is a better term for this material, due to some of this carbon's properties it has been designated vitreous carbon. The vitreous carbon should best be an isotropic for certain manufacturing procedures for microtome knives involving controlled fracture of the material.

Vitreous carbon is a nongraphitic carbon material which may be formed by controlled heating of selected polymeric precursors in accordance with known procedures which generally involve slow carbonization of a formed article under conditions which permit diffusion of pyrolysis products without disruption of the physical integrity of the artifact, and which is generally accompanied by a larger, but predictable contraction in the size of the formed artifact [Jenkens, et al., *Polymeric Carbons—Carbon Fibre, Glass and Char*, Cambridge University Press (1976)]. Vitreous carbon may be produced in a variety of forms, such as a molded sheet form, or a precursor shape such as a scalpel or blade shapes. The molecular structure of the vitreous carbon is believed to involve carbon atoms joined by strong covalent bonds to form relatively small planar hexagonal arrays plus other carbon arrays which are disordered with respect to one another in a turbostatic structure.

The existence of a cross-linked aromatic structure in the original polymer, or during thermal degradation is believed to prevent formation or rearrangement to a full graphite structure on subsequent heating and provides for the turbostatic structure.

Vitreous carbon knife elements in accordance with the present invention should generally be provided from vitreous carbon material having a density of at least about 1.35 g/cc and typically have a bulk density of about 1.45 g/cc. The density will generally be less than about 1.5 g/cc, but it should be noted that the inclusion of carbide forming elements may increase the density of a vitreous carbon material.

The physical properties of the vitreous carbon material are important in the provision of microtome knives. In this connection, the vitreous carbon should have a compressive strength of at least about 90,000 pounds per square inch, and will generally be in the range of from about 90,000 to about 140,000 pounds per square inch. The vitreous carbon should also have a tensile strength of at least about 25,000 pounds per square inch, and will generally be in the range of from about 25,000 to about 35,000 pounds per square inch at 20° C. The material should further have a Young's modulus of at least about $3\times10^6$ pounds per square inch (e.g., in the range of $3-4\times10^6$ psi), and a hardness of at least about 7 on mohs scale. Accordingly, the vitreous carbon material utilized in the knife elements herein is a very hard material which will scratch most forms of siliceous glass. It is further important that the vitreous carbon be highly uniform in structure, and in this connection should best be free of crystalline inclusions, porosity or other structural defects. In this connection, the vitreous carbon should best have a permeability of less than about $2.5\times10^{\times 11} cm^2/sec$ (helium) and a porosity of less than about 0.05. The vitreous carbon materials should be substantially nongraphitic and homogenous in composition and in this connection, the X-ray crystallite size of $L_c$ of the vitreous carbon should best be less than about 26A and more preferably less than about 24A. The thermal conductivity of the vitreous carbon may desirably be at least about 0.01 cal/cm/sec/° C.

As indicated, the vitreous carbon used for knife manufacture by fracture methods is desirably substantially free of crystalline defects, and in this connection, it is desirable to use very high purity polymer precursors which are substantially free of components which induce or provide carbon (graphite) or carbide crystallization. However, the vitreous carbon may be reacted with various carbide forming elements to modify the properties of the vitreous carbon. Such reaction may be carried without substantial graphite formation and the materials may be combined within the turbostatic structure of vitreous carbon without merely forming an external deposit. In this regard, a vitreous carbon knife element may be reacted with carbide forming elements such as silicon, boron, tungsten, tantalium, tianium, zirconium, hafnium, vanadium, niobium, chromium, molybdenum, and mixtures thereof without substantial change in the shape of the knife edge, by selecting a volatile compound (such as hydride) of the carbide forming elements and reacting this compound in the vapor phase with the vitreous carbon microtome knife at a suitably elevated temperature. Laser-controlled diffusion processes may also be utilized.

Figure 1:
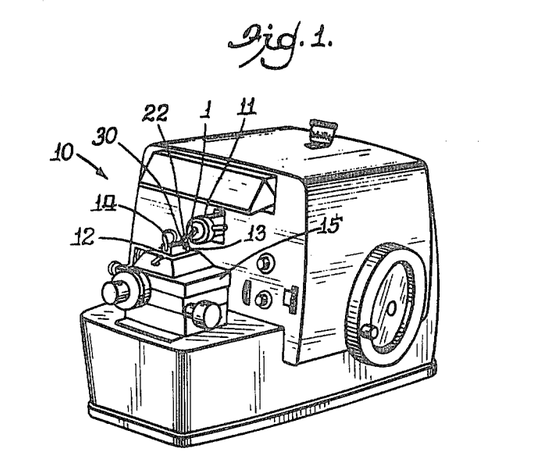
FIG. 1 is a perspective view of microtome apparatus utilizing a knife element in accordance with the present invention.

Turning now to the drawings, various aspects of the present invnention will be more particularly described with respect to the microtome apparatus illustrated in FIG. 1. The apparatus 10 is of generally conventional design comprising an object holder assembly 11 adapted to secure a specimen 1 for sample preparation. The microtome apparatus 10 further comprises a knife holder assembly 12 of conventional design of the type utilized for holding glass and diamond knife elements, and which is adapted to secure in mounted relationship thereto an unconventional knife element 30 of particular specification in accordance with the present invention. The illustrated holder assembly 12 comprises a steel yoke 13 with a soft plastic blunt end which rests against the knife, and provides a slot 14 at its midpoint which is sufficiently wide to accommodate the thickness of the vitreous carbon knife element 30. The vitreous carbon knife element is mounted in the holder assembly 12 between the yoke 13 and knife slot 14 and held in alignment with the yoke 13 when tightened. The knife holder 12, with the vitreous carbon knife in place, is then placed in final knife angle adjustment by being secured to 15 of the ultra microtome. The illustrated vitreous carbon knife element has a substantially linear knife edge 31 of extreme sharpness which has exceptional capacity for sample cleavage. In the illustrated embodiment 10, at least one plane surface 22 of the knife 30 is rendered hydrophilic and a water trough is provided along the surface 22 to float cleaved sample sections off the edge of the knife in accordance with conventional practice.

In operation, the object holder is moved toward the knife element 30 and the sample impacts the knife edge 31 to cleave sample tissues from the sample object.

The sample may be of the organopolymeric impregnated type in which a tissue specimen has diffused thereinto an organopolymeric precursor such as an acrylic monomer or epoxy resin precursor, which is subsequently polymerized to provide a rigid and relatively hard sample specimen for cleavage. The forcing of the object against the edge of the knife element 30 may generate immense pressures and mechanical strains at the knife edge, and the knife 30 must be capable of repeatedly withstanding such conditions. While individual knife elements vary, such conditions normally would require the changing of a cleaved glass knife element after, for example, less than about 10 specimen sample sections of conventional thickness in a range of less than 2 microns and about 5 microns of 2-10 microns thickness. Substantial difficulty may be experienced with conventional glass knives in efforts to cleave samples of greater thicknesses, such as from about 10 to 50 microns in thickness. However, the vitreous carbon knife element 30 readily and repeatedly cleaves relatively thick organopolymeric impregnated specimen samples in the range of from about 10 to about 50 microns of thickness and is utilizable in the cleavage of a relatively large number of specimens, for example, in excess of 100 specimens without a change in quality.

As indicated, the knife elements provided in accordance with the present invention are manufactured of vitreous carbon, and may be provided using slightly modified equipment similar to that used in the manufacture of glass microtome knife elements. In this connection, the microtome knife elements may be manufactured by providing a suitable vitreous carbon sheet having substantially flat parallel surfaces, scoring the sheet along a first line, fracturing the sheet along the first line orthogonally to the parallel surfaces to form a first substantially flat cleaved surface, scoring the sheet along a second line intersecting the first scored line and fracturing the sheet along the second line to form a substantially flat cleaved surface orthagonal to said sheet surface, free of score marks and intersecting the first cleaved surface to form a microtome knife edge.

Figure 2:
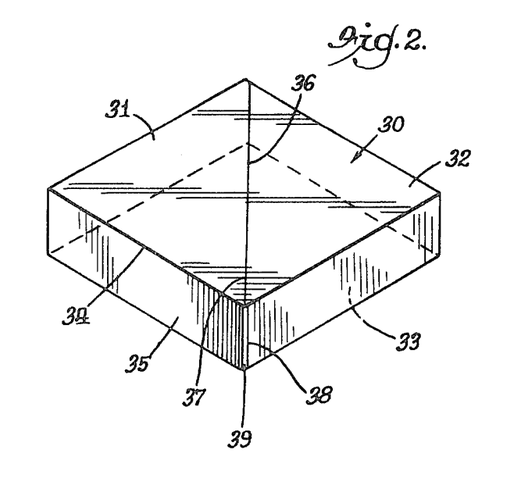
FIG. 2 is a perspective view of the knife element of the microtome of FIG. 1 and another similar element following a controlled fracture step in the manufacture of such elements.

FIG. 2 illustrates in perspective view the knife element 30 which has been broken from a scored vitreous carbon plate 31 having flat, smooth, parallel surfaces 32, 33 and which has previously been fractured along a line 34 to form a substantially planar fracture surface 35 perpendicular to the surfaces 32, 33. The plate 31 is provided from a commercially available VITRECARB vitreous carbon sheet having a thickness of 0.25 inch and a length of about 2 cm. which is manufactured by Fluorocarbon Company of Anaheim, Calif. and has a density of 1.47 g/ml, a permeability of less than $2.5\times10^{-11} cm^2/sec$, a porosity of less than 0.05 percent, a thermal conductivity in the range of 0.01 to 0.02 cal/cm/sec/° C., a compressive strength in the range of 90,000 to 140,000 psi, a tensile strength in the range of 25,000 to 35,000 psi at 20° C., and a Young's modulus of $3-4 \times 6^{10}$ psi. The plate 31 is substantially pure carbon (about 2 ppm impurities) which is substantially free of crystalline carbide inclusions.

Figure 7:
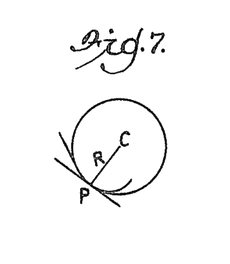
FIG. 7 is a diagram for describing radius of curvature determination.

The plate 31 is fractured along diagonal score line 36 to form a fracture plane 37 which provides a microtome knife edge 38 at its intersection with the fracture plane 35 and leaving a sheld 39 on the opposite triangle. The angle formed by the intersection of the fracture planes 35, 37 is typically in the range of from about 45° to about 55°, but may be varied within a broad range. The intersection 38 of the fracture planes 35, 37 forms an extremely sharp substantially linear edge, which has a radius of curvature of less than about 5 microns. By radius of curvature is meant, the radius of curvature R of a plane curve at any point P (FIG. 7) is the distance, measured along the normal, on the concave side of the curve, to the center of curvature, C, this point being the limiting position of the point of intersection of the normals at P and a neighboring point Q as omega is made to approach P along the curve.

While the illustrated knife edge 38 is manufactured by cleavage techniques as previously described, vitreous carbon microtome knives may be provided by grinding and lapping procedures and polished to produce a very sharp knife edge. The lapping, grinding and polishing procedures may desirably provide slight hollow-ground surfaces for some application, which are considered herein to be smooth, substantially planar edge forming surfaces.

Figure 5:
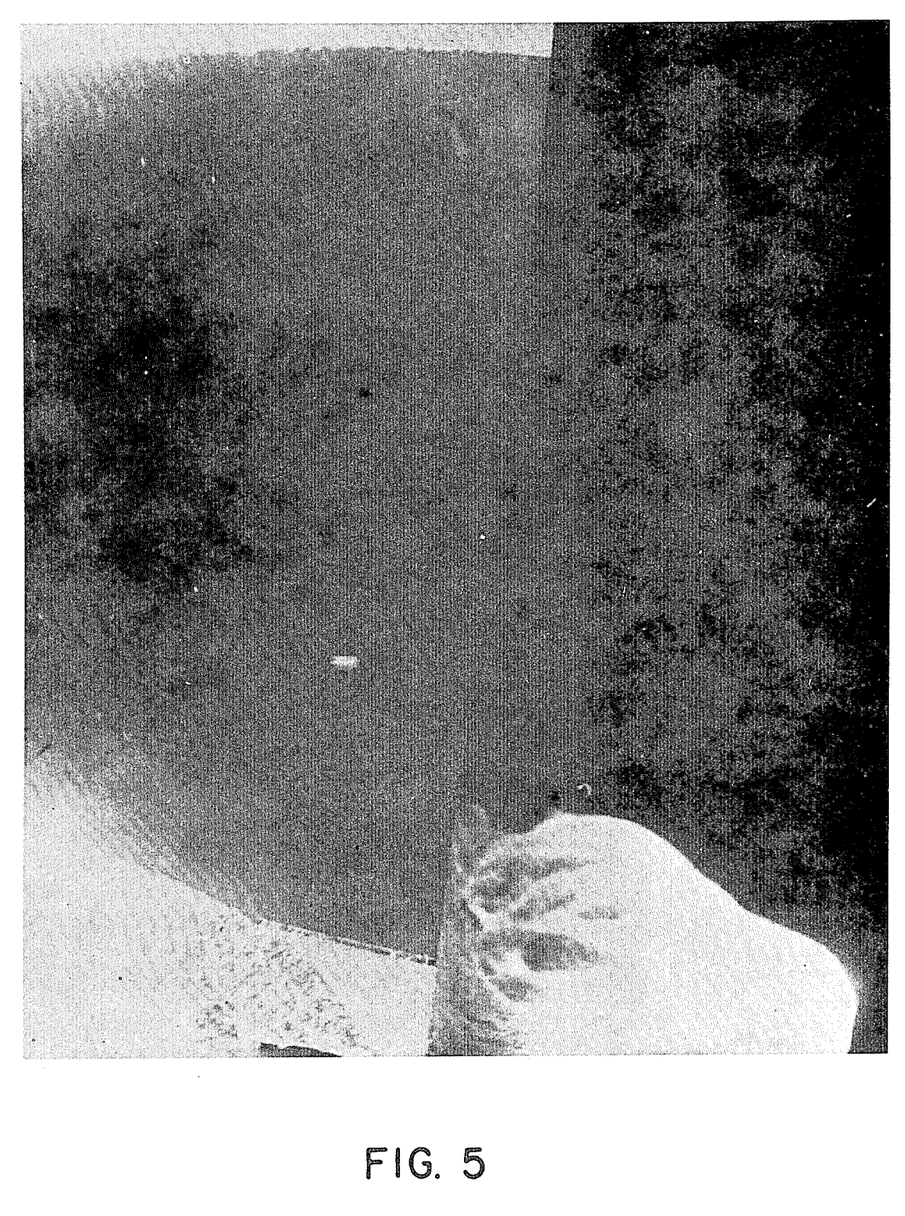
FIG. 5 is a photograph by scanning electron microscope of the cutting edge of a vitreous carbon microtome knife element produced by machining, at a magnification of 27.
Figure 6:
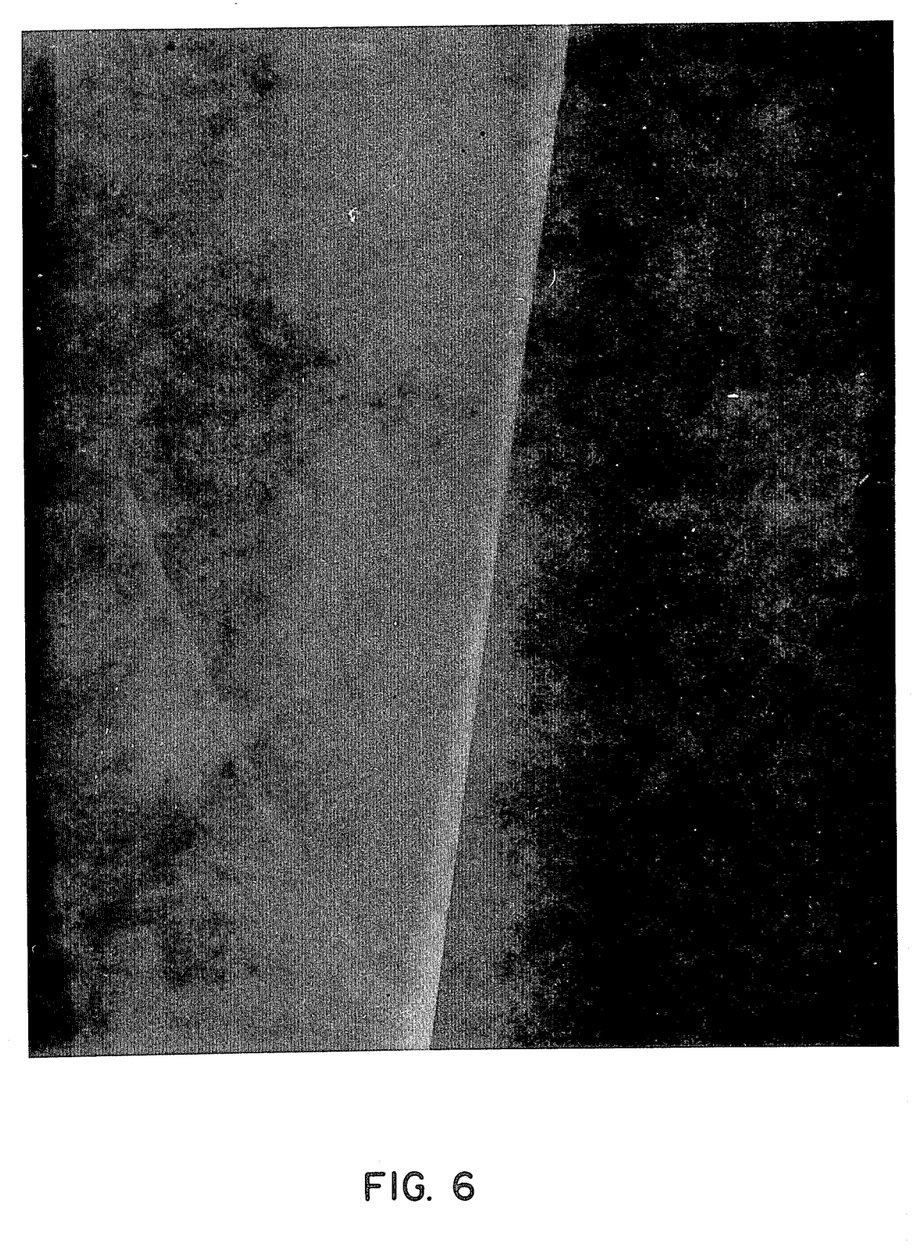
FIG. 6 a photograph by scanning electron microscope of a portion of the cutting edge of the knife element of FIG. 5, at a magnification of 2700, 100 times the magnification of FIG. 5.

In this connection, a vitreous carbon knife is prepared by first cutting a $1'' \times 1'' \times \frac{1}{4}''$ square at 45° angle from corner to corner using a standard mechanical diamond saw to form triangles of equal dimensions. Next, rough grinding is performed on a standard low speed lapping machine to form the cutting edge. This is a step-wise procedure starting with 250 micron diamonds embedded in a metal disk, going down to 15 micron diamonds to achieve a straight, linear edge. Further lapping and polishing is now performed on a standard low speed lapping machine with a further reduction in diamond size, down to 1 micron. The lap used, being made of a soft metal, is prepared in a typical fashion which achieves a straight, linear edge on the vitreous carbon knife. A combination of polishing materials such as silicon oxide and aluminum oxide, together with "carriers" of water, detergents and oils are used to achieve the final edge. FIGS. 5 and 6 are photographs of a knife element produced by the above procedures, which were taken at a magnification of 27 times and 2700 times respectively to show a substantially linear and defect free knife edge. Since all three surfaces of the triangle are lapped and polished, it is possible to produce two cutting edges on one knife, whereas a cleaved vitreous carbon knife only has one cutting edge.

Such procedures may advantageously provide knife edges of substantial length which could be used on histological microtomes which require 25 mm. to 38 mm. knife lengths or longer; while utilization of fracture procedures tends to limit the maximum knife edge length to the thickness of the carbon plate, which in turn is limited by the vitreous carbon manufacturing process.

Vitreous carbon is a hydrophobic material, and in order to provide for use of the knife edge 38 with water for cleaved sample handling in accordance with conventional sample handling techniques, at least one surface adjacent to the edge may be rendered hydrophilic, although it will be appreciated that such treatment should not substantially degrade the knife edge sharpness.

Figure 3:
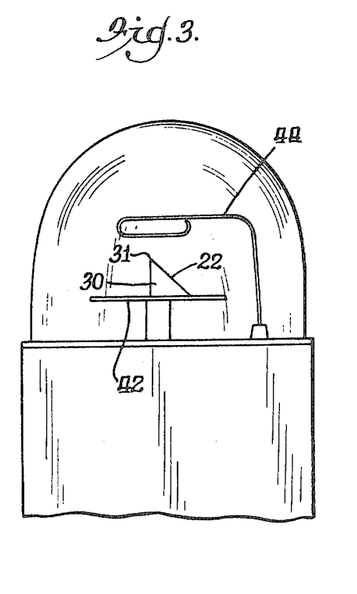
FIG. 3 is a schematic illustration of the knife element of the microtome of FIG. 1, in a manufacturing step subsequent to the fracture step illustrated in FIG. 2.

Hydrophilic properties may be provided by acceptance of the electrostatic charge on the vitreous carbon surface, and in this regard, FIG. 3 illustrates the changing of the surface properties of vitreous carbon knife element 30 by ionization treatment. In this connection, it is important to note that the cutting surfaces of a vitreous carbon knife must be rendered hydrophilic or it becomes almost impossible to use as a sectioning tool. Due to the physical chemistry of the surface, the vitreous carbon attracts and acquires an electronic charge which renders it hydrophobic and unuseable. Therefore one must deionize the surface, as described below, or use other suitable procedures, which may be utilized to treat the vitreous carbon microtome surfaces, if desired. As shown in FIG. 3, the preformed knife element 30 may be placed on the stage 42 in an evacuated chamber (e.g., at a vacuum of 150 millitorr) of a vacuum evaporator using a filament voltage to an ionization probe 44 of about 40 volts for 2-5 minutes to render the microtome surface hydrophilic.

Figure 4:
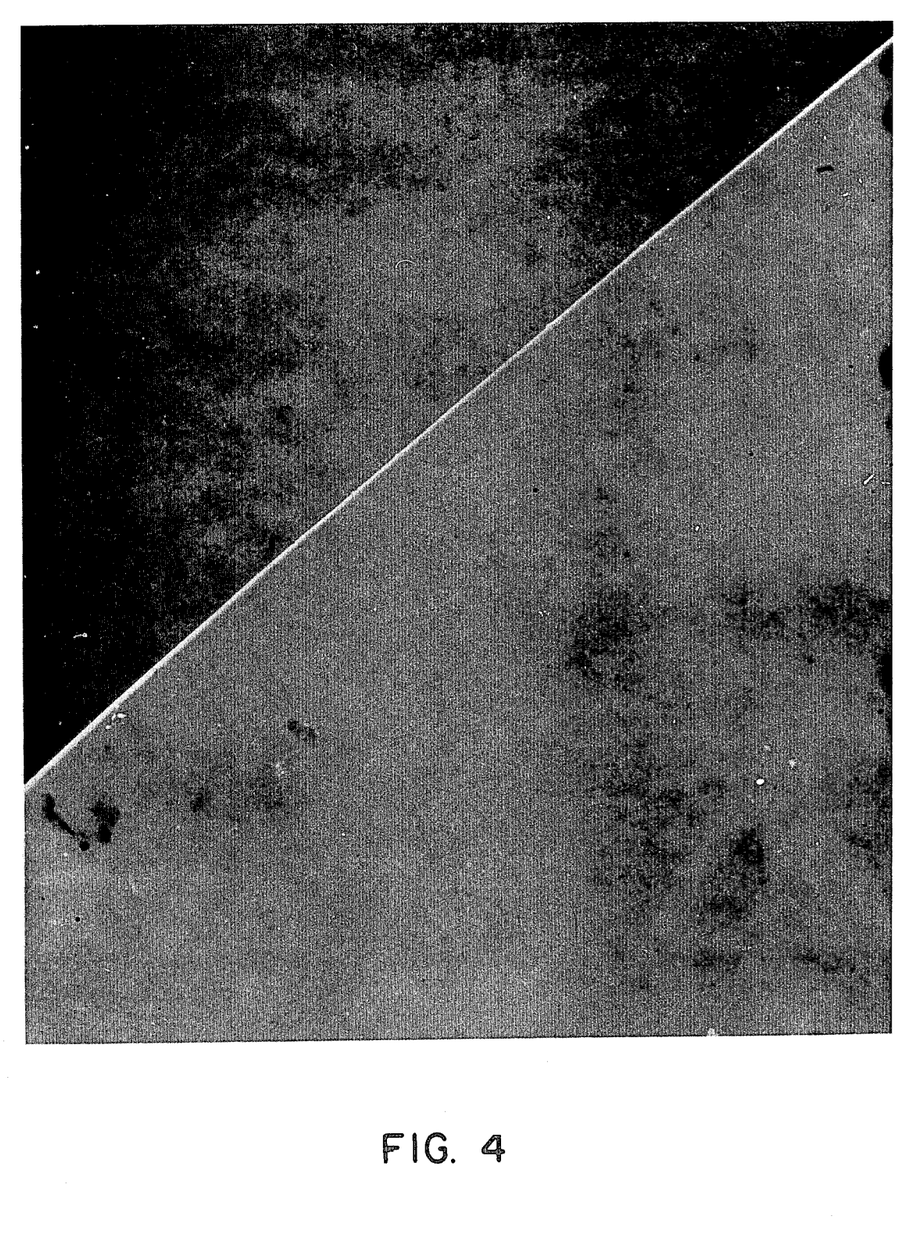
FIG. 4 is a photograph by scanning electron microscope of a portion of the cutting edge of the vitreous carbon knife element of FIG. 1 at a magnification of 540.

In accordance with the present invention, vitreous carbon microtome knives of high sectioning capacity and extreme sharpness may be provided. In this connection, FIG. 4 is a scanning electron microscope photomicropgraph of a portion of the knife edge 28 of the microtome knife 20 following cleavage and ionization treatment. The photomicrograph of FIG. 4 is taken at a magnification of 540 times and illustrates the uniformity of the cutting edge, as well as the sharpness of the edge which may be achieved.

In order to demonstrate the performances of the microtome methods and apparatus in accordance with the present invention, a series of sections of various tissue samples and of varying thicknesses are taken over a period of six weeks using a Sorvall MT-2B UltraMicrotome in which is mounted a vitreous carbon microtome knife manufactured in accordance with the previous disclosure.

The following table presents the data in connection with various runs:

TABLE 1

SECTIONING RUN WITH
HYDROPHOBIC KNIFE ELEMENT
(Knife Not Treated By Ionization)

| Sec. # # | Est. Sec. Thickness (M) | Section Quality | | |
|---|---|---|---|---|
| | | Accept. Publisher Quality | Part Accept. | Unaccept. |
| 1 | Cannot Determine | | | X |
| 2 | " | | | X |
| 3 | " | | | X |
| 4 | " | | | X |
| 5 | " | | | X |
| 6 | " | | | X |
| 7 | " | | | X |
| 8 | " | | | X |
| 9 | " | | | X |
| 10 | " | | | X |
| RUN TERMINATED | | | | |

NOTE:
Due to hydrophobic properties of the knife, quality sections were unattainable.
SPECIMEN TYPE: Anterior angle/animal eye
EMBEDDING MEDIA: Epon (Epoxy resin)

As a comparison, a conventional glass microtome knife is freshly prepared and is used in the microtome. The glass knives are unable to satisfactorily cleave specimens greater than 10 microns in thickness and must frequency be replaced with a new glass knife after taking about 5 full-thickness sections of dimensions in the range of 2-10 microns.

TABLE 2

SECTIONING RUN WITH HYDROPHILIC KNIFE ELEMENT
(Knife Treated By Ionization)

| Sec. # # | Est. Sec. Thickness (M) | Section Quality | | |
|---|---|---|---|---|
| | | Accept. Publisher Quality | Part Accept. | Unaccept. |
| 1 | 4 | X | | |
| 2 | 2 | X | | |
| 3 | 25 | | x | |
| 4 | 10 | | x | |
| 5 | 10 | | x | |
| 6 | 10 | | x | |
| 7 | 10 | x | | |
| 8 | 10 | x | | |
| 9 | 10 | x | | |
| 10 | 10 | x | | |
| 11 | 15 | | x | |
| 12 | 15 | | x | |
| 13 | 15 | | x | |
| 14 | 15 | x | | |
| 15 | 15 | | x | |
| 16 | 25 | | x | |
| 17 | 25 | | x | |
| 18 | 25 | | x | |
| 19 | 15 | x | | |
| 20 | 5 | x | | |
| 21 | 10 | | | x |
| 22 | 20 | x | | |
| 23 | 30 | x | | |
| 24 | 30 | x | | |
| 25 | 15 | x | | |
| 26 | 10 | x | | |
| 27 | 10 | x | | |
| 28 | 10 | x | | |
| 29 | 20 | x | | |
| 30 | 25 | x | | |
| 31 | 25 | x | | |
| 32 | 5 | x | | |
| 33 | 15 | x | | |
| 34 | 20 | x | | |
| 35 | 30 | x | | |
| 36 | 30 | x | | |
| 37 | 30 | x | | |
| 38 | 40 | | | |
| 39 | 40 | x | | |
| 40 | 40 | x | | |
| 41 | 40+ | x | | |
| 42 | 40+ | x | | |
| 43 | 40+ | x | | |
| 44 | 40 | x | | |
| 45 | 40 | x | | |
| 46 | 40 | x | | |
| 47 | 40 | x | | |
| 48 | 40 | x | | |
| 49 | 40 | x | | |
| 50 | 30 | x | | |
| 51 | 30 | | x | |
| 52 | 2 | x | | |
| 53 | 50+ | x | | |
| 54 | 1-2 | x | | |
| 55 | 1-2 | x | | |
| 56 | 1-2 | x | | |
| 57 | 1-2 | | x | |
| 58 | 1-2 | x | | |
| 59 | 1-2 | x | | |
| 60 | 1-2 | x | | |
| 61 | 1-2 | x | | |
| 62 | 30 | x | | |
| 63 | 30 | | | x |
| 64 | 30 | | | x |
| 65 | 20 | | x | |
| 66 | 30 | | x | |
| 67 | 30 | x | | |
| 68 | 30 | x | | |
| 69 | 30 | | x | |
| 70 | 30 | | x | |

NOTE:
At a knife sample age of approximately 5 months it would still cleave acceptable samples.
SPECIMEN TYPE: Same as in Table 1

The deterioration of sectioning capability of the glass knives apparently may represent no more than subtle or small scale changes in the knife structure. In this connection, comparison of a scanning electron microscope micrograph, examined at 540X, of a glass knife after failure through use after cleaving 47 specimens of 1000A-30 micron thickness at which time the knife would no longer thin or thick section. Comparison with a similar micrograph of a glass knife, made immediately after cleaving that knife, does not reveal any substantial differences in the edge appearance in the scanning electron micrograph. On the other hand, vitreous carbon knives may have visible edge defects produced through use, and still be capable of cleaving specimen samples.

As also previously indicated, various aspects of the present invention find particular utility in surgical procedures, both human and veterinary, in which it is necessary to provide smooth, clean incisions in a uniform manner with minimum tissue trauma. In accordance with such surgical aspects of the invention, surgical instruments and methods are provided which utilize a vitreous carbon knife element, which may be, for example, a scalpel blade for major or macroscale incisions, a micro dissection intrument blade for delicate microsurgical techniques, or a specialized blade such as a trephine or coring instrument. The vitreous carbon blades may be provided by grinding, lapping and polishing of a vitreous carbon knife body, as previously described. The blade edge should have a microscopically smooth and continuous cutting edge (along the direction of the edge), and it is a particular adavantage of the vitreous carbon cutting edges and cutting method that edges may be provided which are extremely sharp and microscopically smooth, as shown in the scanning electron microphotograph of FIG. 6.

When performing surgical techniques on a living body, it is necessary to have a readily controllable rate of incision through the surgical site, and it is desired to produce a smooth, clean incision with minimum tissue trauma. However, living tissues, such as corneal tissue, bone tissue, and heart tissue may be quite tough and/or difficult to cut, and accordingly require extremely sharp surgical instruments which retain their sharpness and provide uniform results with use, for most effective surgical techniques.

In accordance with the present invention, vitreous carbon surgical instruments and methods are provided which are extremely sharp, have excellent and uniform cutting characteristics, and which retain their properties over a substantial period of use.

Figure 8:
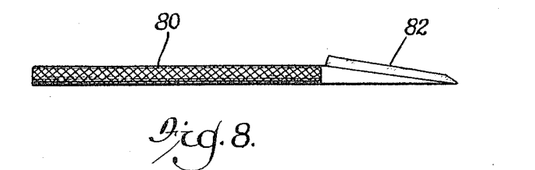
FIG. 8 is an illustration of a one-piece vitreous carbon surgical scalpel.

Vitreous carbon surgical knives may take appropriate form for the particular surgical application contemplated. For example, illustrated in FIG. 8 is a one piece scalpel 80 which is manufactured by forming the scalpel of a vitreous carbon organopolymeric precursor, and heating the formed precursor in a conventional controlled heating cycle to convert the formed precursor material to vitreous carbon having properties as previously described. The blade edge 82 of the scalpel 80 is subsequently ground, polished and lapped to provide an extremely sharp edge as described in respect to the embodiment of FIG. 6 (although it will be at a more acute angle than the cutting edge of FIG. 6). The scalpel 80 may be used in conventional surgical techniques to provide smooth, clean incisions with minimal amount of trauma to the tissue.

Figure 9:
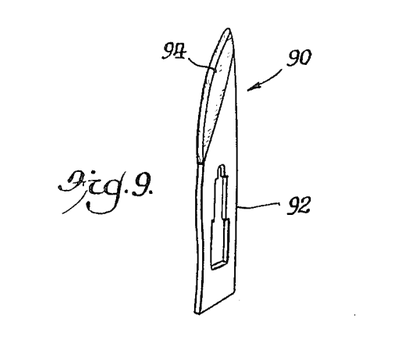
FIG. 9 is an illustration of an embodiment of a vitreous carbon surgical knife blade.

Illustrated in FIG. 9 is a vitreous carbon surgical blade 90 which comprises a base portion 92 of a material such as stainless steel adapted to be affixed to a conventional surgical scalpel handle (not shown) and vitreous carbon blade portion 94 affixed thereto in an appropriate manner such as by means of an epoxy or other suitable adhesive.

Figure 10:
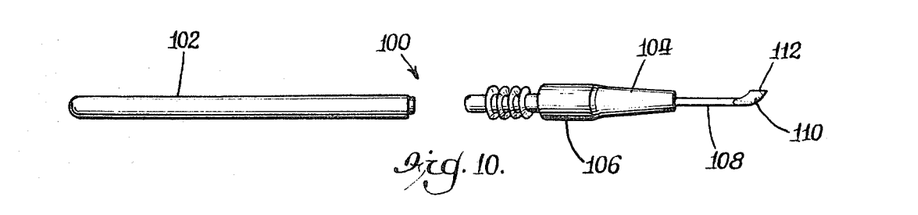
FIG. 10 is an illustration of a microdisection instrument utilizing a vitreous carbon knife edge.

FIG. 10 depicts a micro dissecting instrument 100 illustrating a type of surgical tool which may be utilized for microsurgical techniques. The instrument 100 comprises a conventional stainless steel micro dissection instrument handle 102 having a threaded internal bore for receiving the removable blade head 104, which is shown magnified in respect to the handle 102. The removable blade head comprises a stainless steel base portion 106 into which is inserted and affixed a vitreous carbon blade element comprising a shaft 108 and polished knife surfaces 110 on opposing sides of the shaft 108 which form an extremely sharp and microscopically, smoothly continuous knife edge 112 which is adapted to provide excellent performance in delicate microsurgical procedures. The blade element may be machined, polished and lapped from a larger vitreous carbon element, or may be preformed before heat treatment, with only the blade faces subsequently being ground, polished and lapped.

Figure 11:
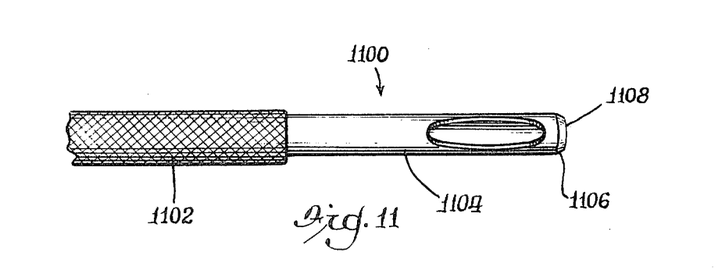
FIG. 11 is an illustration of an vitreous carbon coring or trephine instrument.

Illustrated in FIG. 11, in magnified view, is a coring or trephine instrument 1100 which comprises a stainless steel handle portion 1102 into which is inserted and affixed a hollow cylindrical vitreous carbon cylinder 1104 having a ground, polished and lapped surface 1106 which forms an extremely sharp vitreous carbon circular cutting edge 1108 with the interior surface of the cylinder adjacent the cutting edge 1108 which is similarly polished, but does not form an interior bevel which would inhibit the internal passage of the cored tissue sample.

While the present invention has been particularly described with respect to certain specific embodiments, various modifications, adaptations and variations will be apparent based on the present disclosure, and are intended to be within the spirit and scope of the present invention.

Various features of the invention are set forth in the following claims.

What is claimed is:

1. A method for smoothly cutting a substrate comprising the steps of providing a substrate to be cut, providing a knife element comprising a vitreous carbon body having two intersecting smooth surfaces which intersect along a substantially smooth intersection edge, and pressing said vitreous carbon knife element intersection edge against said substrate to cleanly slice said substrate.

2. A method in accordance with claim 1 wherein said vitreous carbon body intersection edge has a hardness of about 7 mohs.

3. A method in accordance with claim 1 wherein said sample is living tissue and wherein a smooth clean incision is provided in said tissue in a single stroke.

4. A method in accordance with claim 1 wherein said surfaces intersect at an angle in the range of from about 7° to about 35°, wherein said edge is at least about 0.25 cm. in length, and wherein said edge has a radius of curvature of less than about 5 microns.

5. A method in accordance with claim 1 wherein said vitreous carbon has a density of at least about 1.35 g/cm$^3$, a compressive strength of at least 90,000 psi, a hardness of at least 7 on the mohs scale, and a porosity of less than 0.05 percent, and wherein said tissue is corneal tissue, bone tissue or heart tissue.

6. A knife element comprising a vitreous carbon body having at least two intersecting substantially smooth sufaces forming a substantially microscopically smooth knife edge having a length of at least about 2 millimeters and having a sharpness characterized by a radius of curvature of less than about 5 microns.

7. A vitreous carbon surgical knife element in accordance with claim 6 wherein said surfaces intersect at an angle in the range of from about 7° to about 35°.

8. A vitreous carbon knife element in accordance with claim 6 wherein said vitreous carbon has a density of at least about 1.35 grams per cm/sq, a permeability of less than $2.5 \times 10^{11}$, a porosity of less than about 0.05%, a compressive strength of at least about 90,000 psi, a tensile strength of at least about 25,000 psi, and a hardness of at least about mohs 7.

9. A vitreous carbon knife element in accordance with claim 6 wherein the plane surfaces forming the knife edge include a carbide forming element.

10. A method for manufacturing a vitreous carbon knife element comprising the steps of providing a body of vitreous carbon, and forming two smooth intersecting surfaces of said vitreous carbon which intersect at an angle in the range of from about 7° to about 60° along a substantially microscopically smooth, continuous edge having a sharpness characterized by a radius of curvature of less than about 5 microns.

* * * * *